(12) United States Patent
Parekh et al.

(10) Patent No.: US 9,907,588 B2
(45) Date of Patent: Mar. 6, 2018

(54) ORTHOPEDIC DUAL POCKET COMPRESSION PLATE AND METHOD OF SURGERY

(71) Applicant: ORTHOHELIX SURGICAL DESIGNS, INC., Medina, OH (US)

(72) Inventors: Selene Parekh, Cary, NC (US); Brian Hockett, Parma, OH (US); Ellen Pokorney, Minneapolis, MN (US)

(73) Assignee: ORTHOHELIX SURGICAL DESIGNS, INC., Medina, OH (US)

(*) Notice: Subject to any disclaimer, the term of this patent is extended or adjusted under 35 U.S.C. 154(b) by 544 days.

(21) Appl. No.: 14/455,288

(22) Filed: Aug. 8, 2014

(65) Prior Publication Data
US 2015/0045837 A1 Feb. 12, 2015

Related U.S. Application Data

(60) Provisional application No. 61/863,729, filed on Aug. 8, 2013.

(51) Int. Cl.
A61B 17/80 (2006.01)
A61B 17/17 (2006.01)
A61B 17/56 (2006.01)

(52) U.S. Cl.
CPC ...... *A61B 17/8014* (2013.01); *A61B 17/1728* (2013.01); *A61B 17/8047* (2013.01); *A61B 17/8057* (2013.01); *A61B 17/8061* (2013.01); *A61B 2017/564* (2013.01)

(58) Field of Classification Search
CPC .................. A61B 17/8047; A61B 17/809
See application file for complete search history.

(56) References Cited

U.S. PATENT DOCUMENTS

| 3,528,085 | A | * | 9/1970 | Walker, Jr. | ......... A61B 17/8014 52/848 |
| 5,087,260 | A | | 2/1992 | Fixel | |
| 5,534,027 | A | * | 7/1996 | Hodorek | ............. A61F 2/30721 128/898 |
| 5,591,169 | A | | 1/1997 | Benoist | |
| 5,667,510 | A | | 9/1997 | Combs | |
| 5,693,055 | A | | 12/1997 | Zahiri et al. | |
| 5,749,872 | A | * | 5/1998 | Kyle | .................... A61B 17/809 606/293 |
| 5,976,139 | A | * | 11/1999 | Bramlet | ............. A61B 17/1659 606/282 |
| 7,128,744 | B2 | | 10/2006 | Weaver et al. | |
| 7,648,508 | B2 | | 1/2010 | Lutz et al. | |
| 8,182,484 | B2 | | 5/2012 | Grant et al. | |
| 8,187,276 | B1 | | 5/2012 | Zahiri et al. | |
| 8,231,625 | B2 | | 7/2012 | Graham et al. | |
| 8,556,946 | B2 | | 10/2013 | Prandi et al. | |

(Continued)

*Primary Examiner* — David Bates
(74) *Attorney, Agent, or Firm* — Duane Morris LLP

(57) ABSTRACT

An orthopedic plate has a first end and a second end each including a locking screw hole that receives a locking screw and spaced from that hole is a closed compression housing that extends from the bone-facing side of the plate and which receives a compression screw that forms an angle of from about 10° to about 70° with a longitudinal axis of the plate. The first and second compression housings are offset from each other and have opposing openings that face toward each other so as to allow the screws projecting therethrough to have crossing directions.

16 Claims, 8 Drawing Sheets

(56) References Cited

U.S. PATENT DOCUMENTS

| | | | |
|---|---|---|---|
| 8,617,224 B2 | 12/2013 | Kozak et al. | |
| 9,005,255 B2* | 4/2015 | Lewis | A61B 17/8014 |
| | | | 606/281 |
| 9,060,822 B2* | 6/2015 | Lewis | A61B 17/8014 |
| 2002/0045896 A1 | 4/2002 | Michelson | |
| 2003/0060827 A1 | 3/2003 | Coughln | |
| 2004/0143266 A1 | 7/2004 | Kozak et al. | |
| 2005/0171544 A1 | 8/2005 | Falkner, Jr. | |
| 2007/0173843 A1 | 7/2007 | Matityahau | |
| 2008/0015593 A1* | 1/2008 | Pfefferle | A61B 17/8052 |
| | | | 606/282 |
| 2009/0036931 A1 | 2/2009 | Pech et al. | |
| 2009/0076554 A1 | 3/2009 | Huebner et al. | |
| 2009/0021001 A1 | 8/2009 | Strnad et al. | |
| 2009/0210011 A1 | 8/2009 | Den Hartog et al. | |
| 2010/0098757 A1 | 4/2010 | Mukunoki et al. | |
| 2010/0125300 A1 | 5/2010 | Blitz et al. | |
| 2010/0274293 A1 | 10/2010 | Terrill et al. | |
| 2011/0009866 A1* | 1/2011 | Johnson | A61B 17/8014 |
| | | | 606/70 |
| 2011/0295234 A1 | 12/2011 | Donley et al. | |
| 2012/0209334 A1* | 8/2012 | Lewis | A61B 17/8014 |
| | | | 606/286 |
| 2012/0303033 A1 | 11/2012 | Weiner et al. | |
| 2013/0053895 A1* | 2/2013 | Stoll | A61B 17/8028 |
| | | | 606/279 |
| 2013/0096629 A1* | 4/2013 | Rollinghoff | A61B 17/80 |
| | | | 606/281 |
| 2014/0148859 A1* | 5/2014 | Taylor | A61B 17/8061 |
| | | | 606/282 |
| 2014/0277176 A1* | 9/2014 | Buchanan | A61B 17/8061 |
| | | | 606/281 |

* cited by examiner

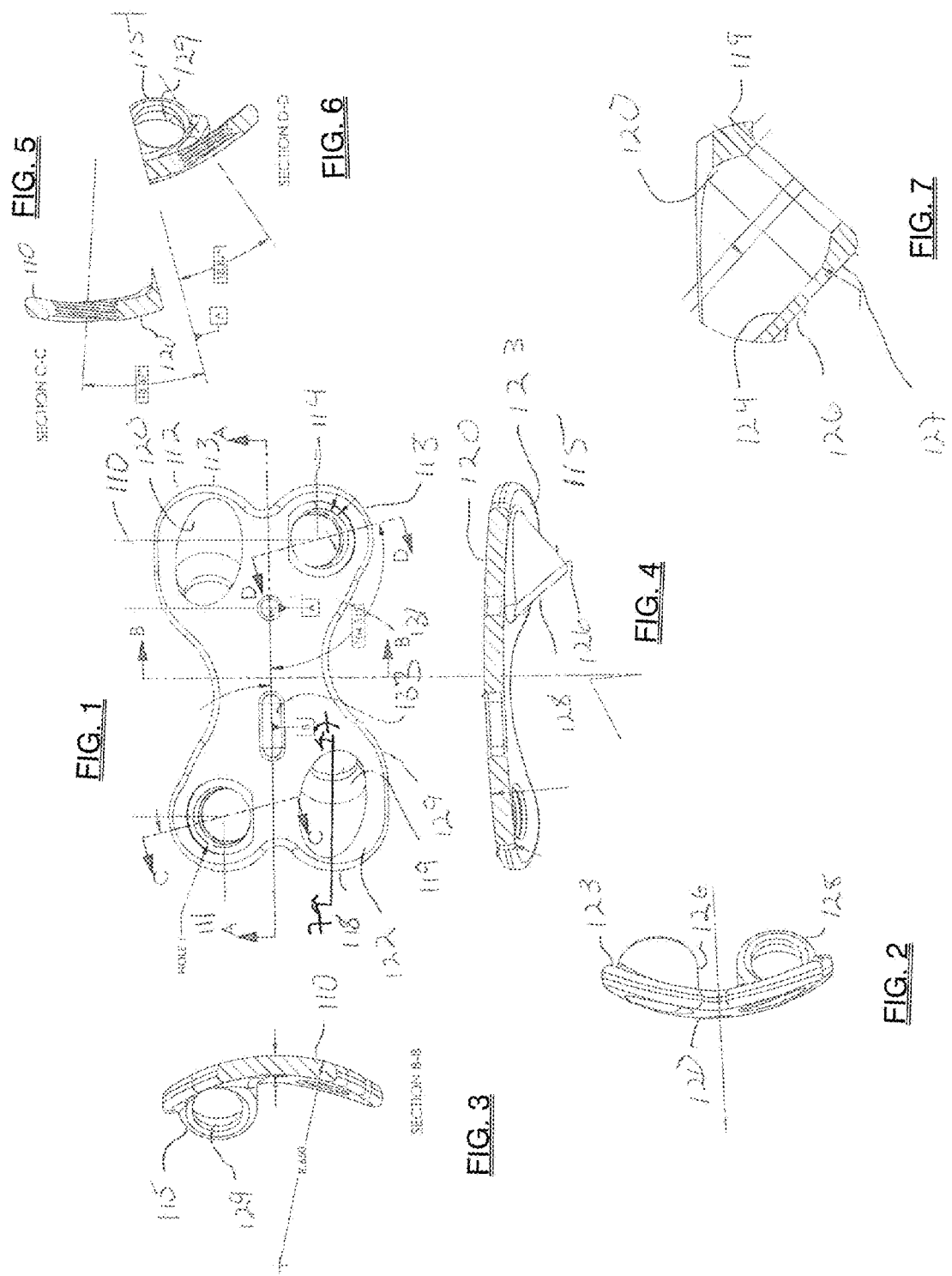

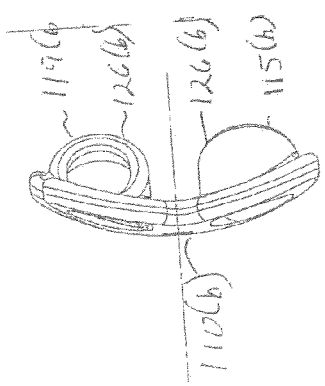
FIG. 8
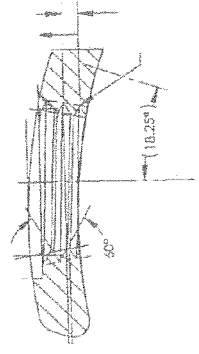
FIG. 10
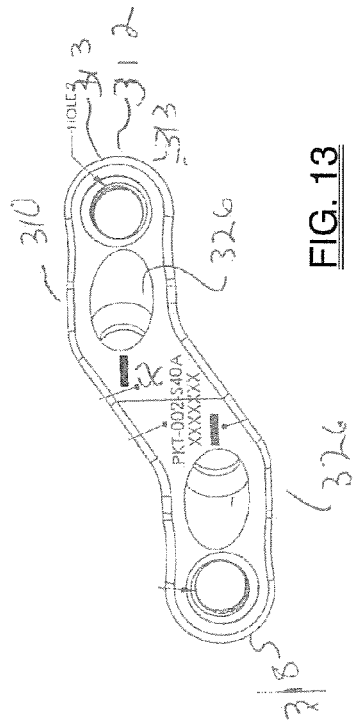
FIG. 9
FIG. 11
FIG. 13
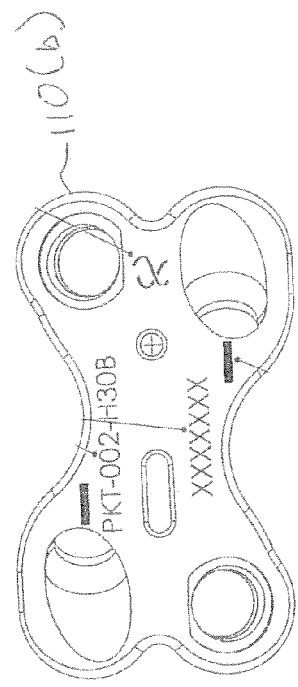
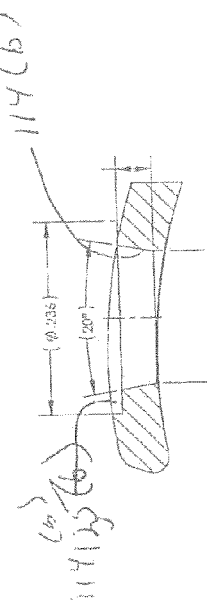
FIG. 12
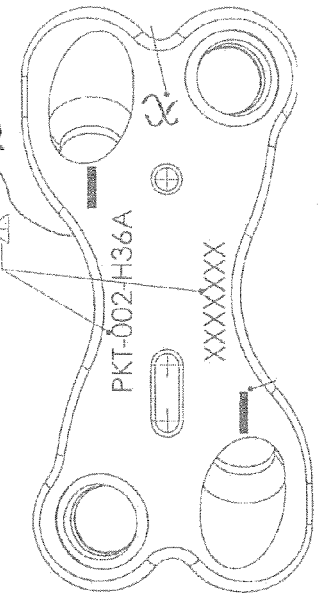

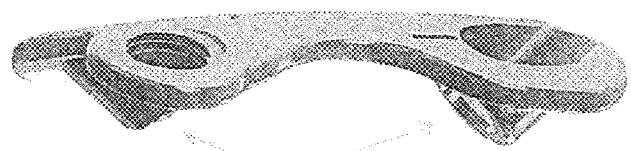
FIG. 21(a)
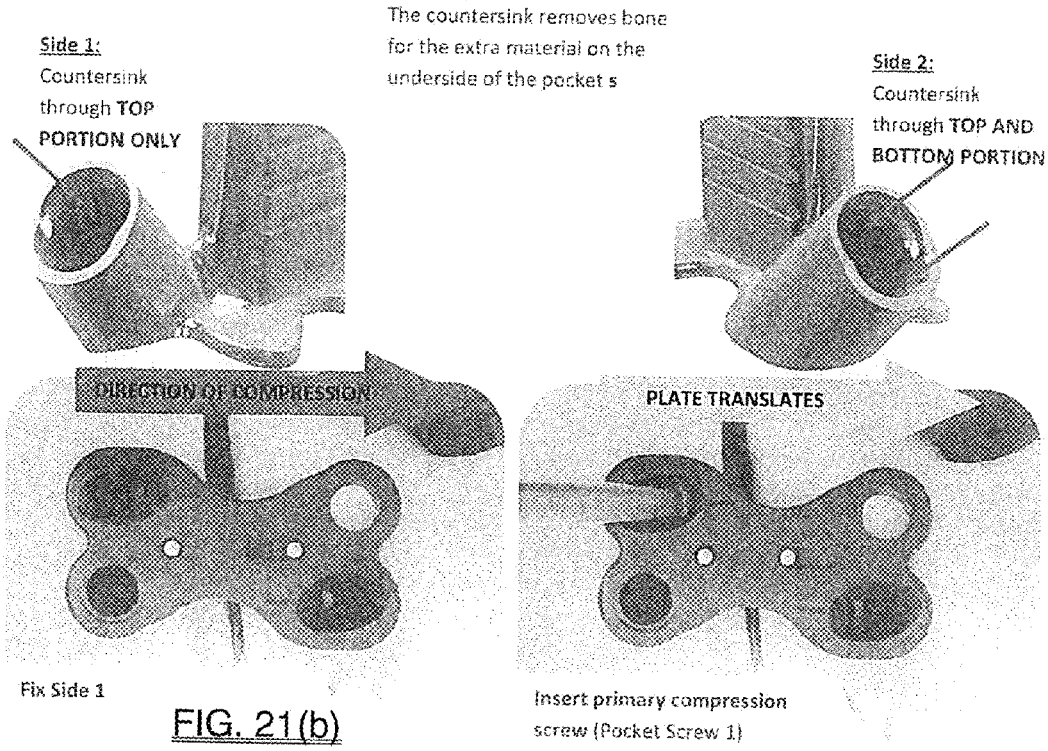
FIG. 21(b)
FIG. 21(c)
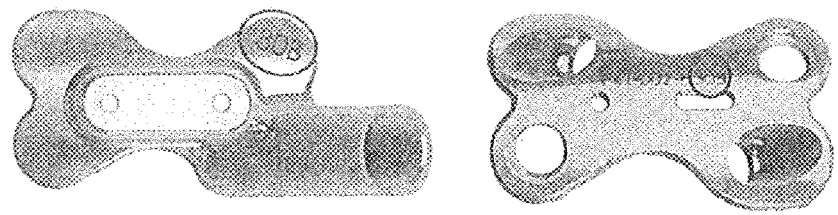
FIG. 21(d)

SECTION A-A
SCALE 5 : 1

ORTHOPEDIC DUAL POCKET COMPRESSION PLATE AND METHOD OF SURGERY

CROSS REFERENCE

This Application claims the benefit of priority under 35 U.S.C. § 119 of U.S. Provisional Application Ser. No. 61/863,279, filed on Aug. 8, 2013, herein fully incorporated by reference.

FIELD OF THE INVENTION

The present invention relates to an orthopedic plate, which is configured to increase compression as well as stability at a bone interface, in particular to stabilize bones or bone fragments relative to each other such as to cause fusion. Specific embodiments and methods of fixation are presented for fixation of the small bones in the foot and arm including, for example, stabilization of a fracture, dislocation or reconstruction of a deformity, such as use in surgeries to correct the flat foot deformities.

This plate has multiple compression structures which house obliquely extending screws and which are located in opposition. The angle of the axis of the oblique screw is from about 10° to about 70°, more specifically about 25° to about 60° and most specifically about 30° to about 45° degrees to a longitudinal axis of the plate which dissects the compression opening on the plate. Thus these screws act as an inter-fragmentary screw while the plate augments the stabilization and compression that is achieved by having traditional screw holes (i.e. which pass through the thickness of the plate at 90°, or substantially normal to the thickness of the plate so that the force component is transmitted mostly in the direction through the plate toward the bone and not in the direction of the bone). These traditional screw holes allow the plate to be fixed to the bone fragments while the compression is achieved using the compression screws. In a further embodiment, the invention relates to a surgical method using the dual pocket compression plate of the present invention.

BACKGROUND OF THE INVENTION

The present invention is designed to combine the compression generation of a cross-screw with the bending and torsional strength of a plate. Thus, the present invention offers a unique and versatile plating option for fixation and stabilization such as for fusion surgeries for various bones in the lower leg and arm. These plates feature a contouring intended to fit a variety of anatomic sites, while creating a low-profile construct and reducing the need for intra-operative plate bending. The invention is applicable as well to application specific plates which are designed for a particular anatomical location and surgical purpose.

These plates feature multiple compression housings or "pockets", which each accepts an obliquely extending screw. This allows a surgeon the option to compress across a fracture or bone interface with a first pocket screw, then gain additional targeted inter-fragmentary fixation using a second pocket screw. Both pockets are designed to provide targeted insertion of suitable screw, such as a 4.0 mm inter-fragmentary screw, through the plate and across the joint or fracture line. The plate is designed to allow for multi-planar fixation with a set of inwardly angled (relative to the plate midpoint) screws and a set of more traditionally placed locking screws (or variably angled locking screws) that help to hold the plate relative to the bones. The present design is meant to reduce the risk of hardware collision associated with supplementary cross-screw insertion outside of a plate. In accordance with the invention, these plates are not right- or left-side specific, but are offered in Alpha™ and Beta™ versions (which are mirror images), designating pocket position and direction of compression. The plates in accordance with the invention are provided in a set or "surgical tray or caddy" which includes specialty instrumentation such as a countersink having a compound opening, which accommodates the underside compression pocket as the pocket screw is inserted and compression is achieved. Thus, these instruments aid in simple and accurate plate and screw insertion. In addition, the plates of the invention generally include threaded screw holes as the usual screw holes which accommodate either non-locking, fixed-angle locking and variable-angle locking screws for selective fixation without compromise of the mechanical properties of the type of fixation.

The present invention combines the advantages of the prior art screw/pin fusion methods with the advantages of a plate, and allows the surgeon the option of using multiple inter-fragmentary or fusion compression screws in a procedure that also incorporates a plate and thus provides the advantages of stress shielding and force loading or balancing that permits earlier weight bearing. Templates are provided which facilitate the operative procedure, including alignment which can remain in position during placement of the plate, counter-boring the surgical site to accommodate the compression screw housings and placement of the "inter-fragmentary" or compression screws. Further, the plate includes elongated wire and/or screw holes that allow for the compression and attendant relative bone movement during the surgery by the engagement of the compression screw. The compression screw or screws are placed in the plate so as to minimize the possibility of interference with the guide wires and traditional plate screws. The openings in the plate for the compression screws are provided so as to allow for opposing inter-fragmentary screws. They generally are offset from each other along the long direction of the plate. This allows a placement of a compression screw that exerts a force on a diagonal to the long axis of the plate (i.e. a compound force relative to the plate having a greater horizontal force component than is traditionally used to hold a plate relative to the bone). Further, these compression housings or "pockets" are provided so as to project below the bone-facing surface of the plate where the pockets provide a closed or sheltered screw/plate interface and the external surface of the pockets can also bear against the bone to help provide a compressive force. The pockets include a slotted opening for the compression screw. Thus, the screw can be angled with a single degree of freedom (i.e. linearly) with respect to the axis of the compression screw hole in the housing.

When proper technique is followed, the first pocket screw will generate compression across the joint. As is the case with any pocket plate, the plate must first be fixed on the same side of the joint as the pocket screw. As the first pocket screw is inserted, the bone will translate (compress) towards the unfixed aspect of the joint. In order for the plate to remain flush against the bone during compression, the empty pocket (or second pocket) must have space to slide within the prepared bone. The instruments provided are used to "over-countersink" for the second pocket screw, which allows the plate to translate within an over-sized bore, while maintaining a low-profile fit on the bone.

SUMMARY OF THE INVENTION

In accordance with the present invention an orthopedic plate is provided that achieves improved compression through the use of a screw that is situated with its axis obliquely to the spine of the plate (i.e. to the longitudinal axis in the plane of the plate taken at the medial line of the plate or alternatively at the medial line of the opening of the compression opening of the plate). The term "spine" of the plate is used to mean a line or curve that is generally medial to the mass of the plate, taking into account that the plates of the invention are somewhat more long than wide, but are amorphous in profile, and have end sections that are may be asymmetrically lobed or tabbed with semi-circular conjoined tabs including screw holes that can have internal threads for locking screws. In a first embodiment, the plate has an outline that is a generalized X-shape having an elongate central trunk which has a length that is roughly one fourth to one third of the total length of the plate, depending on where one considers that the trunk ends and the terminal screw holes begin. The trunk narrows at the mid-line and flares outward at each end into two conjoined tabbed portions which each include a screw hole to accommodate a traditional plate screw on one lateral side and a compression pocket on the other. For example, the distance from the mid-point of the compression slot to the other compression slot might be about 14-18 mm for a 30 mm plate, and the narrowest portion might be 6-8 mm, with a widest point at the screw holes of from about 17 to about 20 mm. In a longer version of the plate, the central distance might be about 5 to 7 mm more. Opposing longitudinal sides share one traditional plate screw and one compression screw. In the center, the plate includes a 3-5 mm slot along the medial line for a k-wire which is elongated to provide for the compressive movement, and across from that there is a hole for a k-wire.

In a further embodiment, the plate profile has two elongated tabs that include a terminal rounded section that is appropriately sized to accommodate a plate screw and interior to that has an opening for a compression screw with a compression screw pocket on the bottom side. A diagonally extending middle section extends from one tabbed end to the other with has mirror symmetry across the midline of the plate. The middle section is from about 8 to about 10 mm for a 40 mm plate. The opening for the compression screw is about 8 (i.e., 7 to 9) mm on the exterior (or superior) surface of the plate. The width is a similar dimension, or about 8.5 mm at the long axis of the mid-section and the compression screws form an angle of about 30-40° relative to the long axis of the tabbed end sections. In this embodiment, the plate may also include small ears including holes for k-wires, positioned approximately exterior to the midline between the two end screw holes.

Preferably the traditional screw holes include a counterbore at the superior opening to the screw hole, which provides a radial flat surface to help define the angle of the plate screws relative to the plate and assure a proper angle to allow the threads of the screw head to engage the threads of the screw holes. These screw holes are internally threaded or provided with other means of fixing the relationship between the screw and the plate independently of the relationship between the distal threads and the bone.

Preferably, the compression screws are received in a housing or pocket which includes an opening in the top surface of the plate and a shroud or boss which extends from the bottom surface of the plate so as to define a pocket on the bottom of the plate that captures the screw at a variable orientation. The housing extends through the plate to accommodate the entire diameter of the head of the screw (i.e. so that the head of the screw does not project significantly or at all beyond the top of the plate when the screw is fully implanted within the plate). However, the pocket is also formed to position the torque driving recess of the screw as close as possible to the top surface of the plate. Thus, the pocket forms a recess that on its short side (viewed in cross section taken along the long medial axis of the opening as shown in FIG. 27), is just deep enough so that the screw head does not project beyond the plate. In other words, the pocket is angled into the plate so that it has a short side wall taken at the shortest point which is only marginally longer than the depth of the screw head (i.e. by +/−25%, 10%, or 5% of the depth of the screw head) from the neck where the head joins the screw major diameter to the top surface which includes the torque driving surface. An opposite internal side wall of the pocket guides the screw head into the pocket and helps to define the angle of the screw axis relative to the axis of the screw hole formed by the pocket. Thus, the screw head does not project beyond the top surface of the plate when the screw is fully seated in the housing. (By "top" it is meant herein the exterior facing surface, which is opposite through the thickness of the plate from the bone-facing surface, of the plate when the plate is in position on the bone. It is understood that the orientation relative to the ground is dependent on the orientation of the plate in space, and therefore that is not relevant in determining what is "top" in this case). The housing also includes an opening on the bottom of the plate through which the screw extends and which is smaller than the diameter of the screw head so as to capture the screw in the housing. The compression screw housings or "bosses" have a generally cylindrical opening terminating in an elongated opening (i.e. an oval) that has a narrowed area from the opening to hold the compression screw head in the housing and where the elongation in the opening allows the compression screw to be translated in one direction or angulated in the plane that bisects the opening. The bottom of the compression opening is circular in cross-section and it provides a compression screw axis that is at from about 10° to about 70°, preferably from about 25° to about 60°, and more preferably about 30° to about 45° relative to a longitudinal axis of the plate which dissects the compression opening on the plate.

Also the housing is slightly larger than the bottom opening so that the convexly rounded screw head has some play in the pocket to allow some freedom of angulation (i.e. about 5 to about 30°, preferably about 10 to about) 20° of conical or modified conical rotational freedom of the screw relative to the housing axis (as measured from the groove formed through the compression opening.) In a further embodiment, the opening is elongated or is a slot, which allows the screw to be placed at a linear variable angle (that is a restricted portion of the conical angulation) relative to the housing, where the amount of angulation is about +/−12°, preferably +/−10°, and more preferably +/−6° of linear freedom relative to the axis of the housing. The angle of the axis of the oblique screw is from about 10° to about 70°, more specifically about 25° to about 60° and most specifically about 30° to about 45° degrees to a longitudinal axis of the plate which dissects the compression opening on the plate (i.e. the "spine of the plate"). A compressive force is applied to the bone or bone fragments by the plate as the oblique screw is screwed tighter and the screw head compresses into an increased fit with the pocket, and in particular with the pocket bottom opening. This draws that bone segment into which the compression screw is screwed, toward the locking screw or screw in the other end of the plate and accordingly, into compression with the bone segment into which the screws associated with the other end of the plate, are screwed.

The plate of the invention includes at least two compression housings as previously described that accept a screw which extends toward the first end of the plate with its axis at an oblique angle of about 10° to about 70°, more preferably about 25° to about 60°, and most preferably about 30° to about 45° with respect to the longitudinal axis of the plate. Further, the bottom surface of the plate is radiused. This allows the plate to be in snug contact with the bone. The housing has an internal recess that houses the compression screw and which has a narrowed opening, that is smaller than an associated screw head so as to capture and retain the screw, but which allows for either linear or conical rotation in the compression housing.

BRIEF DESCRIPTION OF THE DRAWINGS

FIG. 1 is a top plan view of an alpha version of the first embodiment of the orthopedic dual pocket compression plate in accordance with the present invention;

FIG. 2 is a right side view of the orthopedic plate of FIG. 1;

FIG. 3 is a cross-sectional view of the orthopedic plate of FIG. 1 taken at line 3-3;

FIG. 4 is a cross-sectional view of the plate of FIG. 1 taken at line 4-4;

FIG. 5 is a cross-sectional view of the plate of FIG. 1 taken at line 5-5;

FIG. 6 is a cross-sectional view of the plate shown in FIG. 1, taken along line 6-6;

FIG. 7 is a cross-sectional view of the plate of FIG. 1 taken at line 7-7;

FIG. 8 is a top plan view of an beta version of the first embodiment of the orthopedic dual pocket compression plate in accordance with the present invention;

FIG. 9 is a right end view of the plate shown in FIG. 2;

FIG. 10 is a detail of the plate screw hole of the plate of FIG. 8 prior to threading;

FIG. 11 is a detail of the plate screw hole of the plate of FIG. 8 after threading;

FIG. 12 is a top plan view of a variation of the first embodiment of the plate of the present invention;

FIG. 13 is a top plan view of a second embodiment of the plate (alpha version) of the present invention;

DETAILED DESCRIPTION OF THE INVENTION

Figure 15:
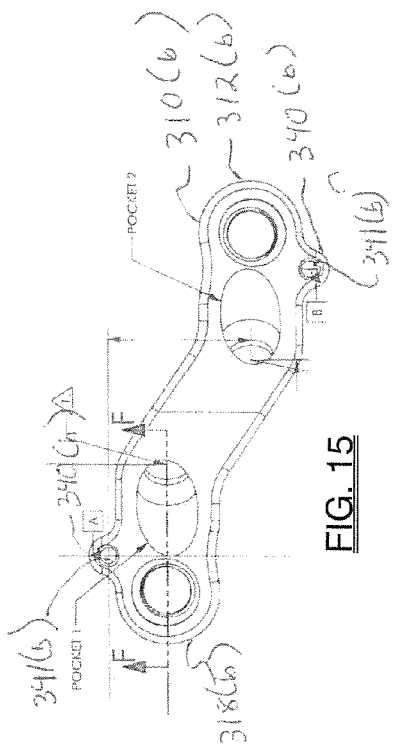
FIG. 15 is a top plan view of a beta version of the embodiment of the plate shown in FIG. 13 with k-wire holes.
Figure 14:
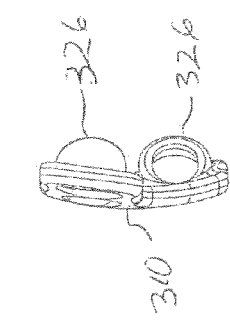
FIG. 14 is a right end view of the plate shown in FIG. 13.

FIGS. 1-7 show an alpha version of the first embodiment of the plate of the present invention. As an example, this plate can be used for surgical correction of flat foot deformity, which involves the fusion of the cuboid and the calcaneus with distal to proximal compression. The plate 110 has a first end 112 and bilaterally symmetrical second end 111, each of which is bi-lobed, or has two conjoined rounds tabs 113,118, of just appropriate size to form mounting rings for threaded locking holes 114 on one side and for the housing or shroud 115, 119 which receives the obliquely extending compression screws. The end tabs extend longitudinally to approximately the same length, but since the surface openings for the locking screw holes and the compression screws vary in shape, the outline of the plate varies on the lateral sides to accommodate these openings. For example, since the compression screw lies at an angle that is not normal to the plate surface, the opening is elongated to "just" accommodate the screw head laid sideways in the opening (one side of the screw head resides just at the screw hole opening and the opposite side dips below the bottom side of the plate, but is held in the obliquely extending pocket). Consequently, the tab has a slight flat on its lateral edge to accommodate the extra length. The plate screw hole tabs form a portion of a circle and mirror the shape of the screw hole opening so as to form mounting rings for the screws which resist deformation in the event that the plate is re-contoured during surgery. While the holes are placed more or less at the same distance longitudinally from the mid-line of the plate, the actual openings are longitudinally and medially offset from each other. The effect on the placement of the screws in use can be seen in FIG. 21(*v*) which shows the two compression screws angled in a "crossed" direction so as to improve the compression across the joint, but laterally offset from each other just sufficiently to inhibit the possibility of impingement while still allowing some variability in the actual placement of these screws. The plate screws extend from the plate in a substantially perpendicular position, although it can be seen that they angle toward each other distally by about 0 to about 12°, and more preferably by about 5° to 10°, and most preferably by about 7° to 9° off of a parallel orientation. This feature improves the purchase in the plate, and inhibits screw backout.

Figure 27:
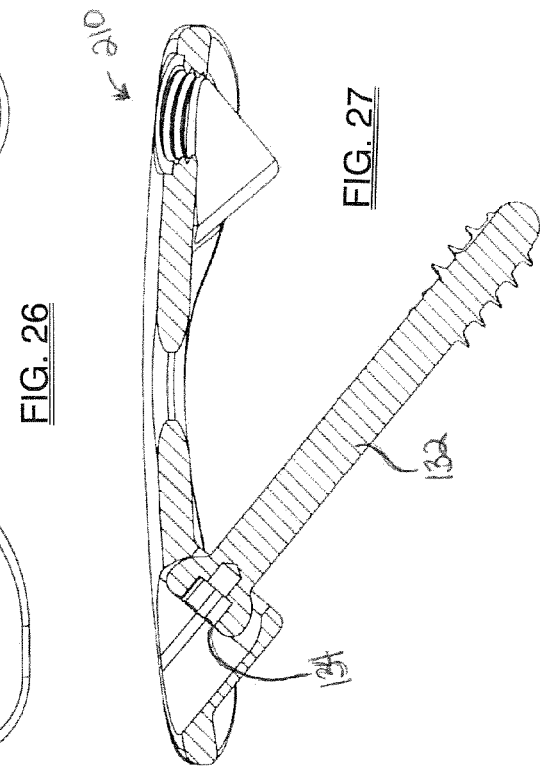
FIG. 27 shows a section of the plate and compression screw.

The compression housing 115,119 includes an opening 120 in the top surface 122 of the plate. The opening 120 is ovoid, with a width that wide enough to accept the compression screw 132 that is received in the opening 120. The compression screw is of slightly greater diameter and of greater length than the locking screws. The opening 120 angles into the top surface 122 of the plate 110 so as to form a groove 124 that accommodates and guides the screw 132 and a mating driver as the screw is screwed into the bone below the plate. On the bottom surface 123 of the plate 110 there is a shroud 126, which has a cylindrical rear surface 127 joined to flat front surface 128. The term "shroud" as used herein means that the housing creates a "pocket" of enclosed space for the compression screw head, which is closed to the bone surface and/or to the motion that can occur between the compression screw and the housing, and in which the structure that defines the enclosed space is connected at each side to the bottom of the plate. The "pocket" forms a 3-dimensional space of a width to accommodate the rounded head of the corresponding screw which projects at a variable angle through the necked opening on the bottom facing surface of the obliquely angled pocket, the pocket external structure is essentially flush at the short wall with the plate bottom surface and extends below the plate bottom surface at the long wall of the pocket external structure. In cross-section as shown in FIG. 27, the pocket resembles a front slash pocket in a pair of trousers. In this instance, the pocket opening face is substantially directly joined to the plate bottom, and does not include any appreciable length between the plate bottom and the edge of the pocket bottom surface. This reinforces the housing structure, helps to create additional compression and closes the housing from the possibility of tissue interference or in-growth. The "housing" comprises a more complete structure than a flat solid rib which projects from the bottom surface of the plate and includes a screw hole (threaded or not). The shroud 126 includes a lower opening 129 which is circular or oval, and which is large enough to allow the major diameter of the screw to pass through, but which is smaller than the diameter of the rounded portion 134 of the head of the screw 132. The compression housing 126 accepts a screw 132 which extends toward the first end 112 of the plate with its axis at an oblique angle of about 5° to about 40°, more preferably about 10° to about 30°, and most preferably about 15° to about 25° with respect to the longitudinal spine of the plate. The bottom surface of the plate is radiused at a constant curve so that the plate forms a portion of a cylinder or alternatively the plate can be radiused in two directions so as to form a portion of a torroid or sphere, or the curves may be more complex, depending on the intended application of the plate. The plate also includes a first circular opening 131 for a k-wire, and also aligned therewith on the longitudinal medial line of the plate is a slot 133, which enables a k-wire to slide relative to the plate as the compression screws are tightened and compression is applied at the bone interface.

FIGS. 8-11 illustrate a second version of the dual pocket compression plate shown in FIGS. 1-7. These FIGS. illustrate the mirror image, or "Beta™" version of the Alpha™ plate shown in FIGS. 1-7. This plate 110(*b*) is a mirror image of the first plate which allows for compression in the opposite direction relative to the first and second ends of the plate. FIG. 9 illustrates the end view of the plate 110(*b*), showing the first shroud 115(*b*) and the second shroud 119(*b*) on opposite sides of the longitudinal axis of the plate from the Alpha™ version.

FIGS. 10 and 11 illustrate the countersink 135(*b*) that is provided in the screw hole 114(*b*) which helps to define the angle for the screw axis by providing a seat for a screw drill guide, and in order to provide a screw angle which permits the threads on the head of a locking screw to properly mate with the internal threads in the locking screw hole 114(*b*). FIG. 12 illustrates a further version 210 of the dual pocket compression plate in which the middle section or trunk is longer.

Figure 18:
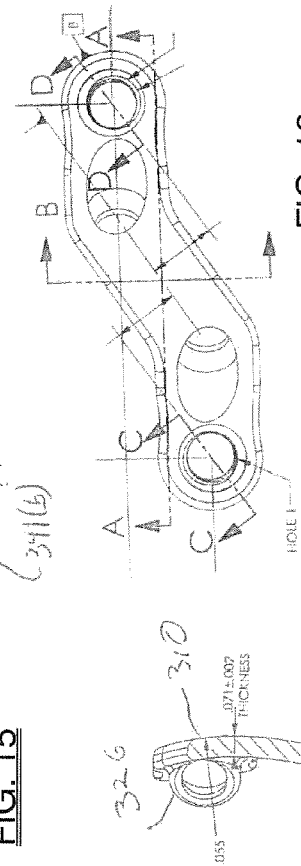
FIG. 18 is a top plan view of the beta version of the plate shown in FIG. 13.
Figure 17:
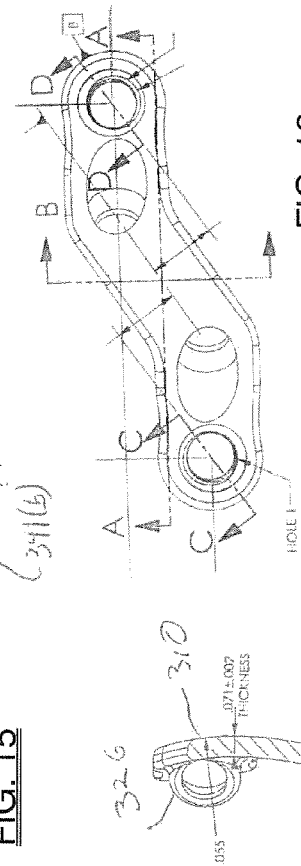
FIG. 17 is a cross-sectional view taken at line 17-17.
Figure 16:
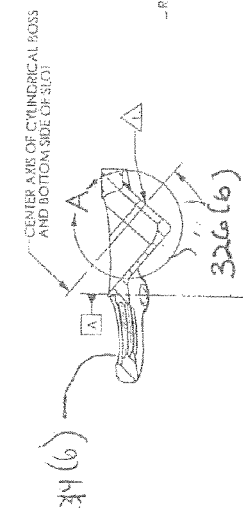
FIG. 16 is a cross-section of the plate shown in FIG. 15 taken at line 16-16.
Figure 19:
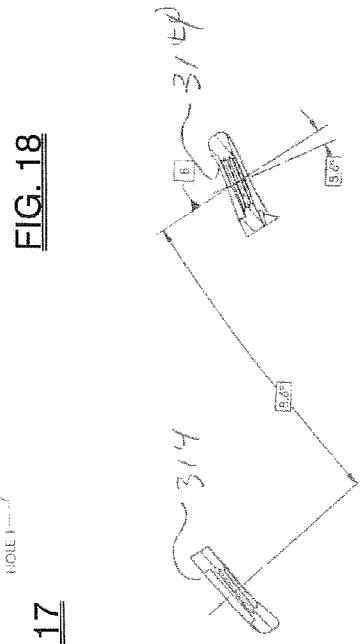
FIG. 19 shows cross-sectional details of the plate holes of the plate shown in FIG. 18 taken at line 19-19.
Figure 20:
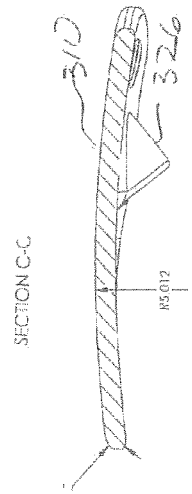
FIG. 20 is a shows cross-sectional details of the plate holes of the plate shown in FIG. 17; taken at lines 20-20.

FIGS. 13-20 illustrate a second embodiment of the dual pocket compression plate in both Alpha™ and Beta™ versions of the plate. In FIG. 13, the plate 310 is shown having a generally S-shaped configuration, which is limited to two terminal ends. Thus, the plate 310 has a first end 312 and bilaterally symmetrical second end 311, each of which is has a single round tab 313, 318, of just appropriate size to form mounting rings for threaded locking holes 314. These terminal ends are also long enough along their length to accommodate the oval opening for a compression housing 326 for each side. These compression housings correspond to those provided in the first embodiment, and the earlier disclosure is descriptive of these as well. In this embodiment, the "central trunk" is an obliquely extending linking section having two edges that extend in the direction of the axis of the linking section parallel to that axis, and to each other. The compression shrouds open toward each other, but are laterally offset so as to inhibit compression screw impingement. FIGS. 15 and 16 illustrate a Beta™ version 310(*b*) of the embodiment shown in FIGS. 13 and 14 and further including small peripheral ears or tabs 340(*b*) on the outside (i.e. lateral side) of the plate having circular holes 341(*b*) to receive k-wires during the surgical procedure. FIG. 16 shows a cross section illustrating the shroud opening 326(*b*) and threaded plate screw hole 314(*b*) on one side The end tabs extend longitudinally to approximately the same length, on either side of the medial axis of the plate. FIG. 17 illustrates a cross-section of the plate taken at the medial axis, while FIG. 18 is a compound cross-section taken through the medial axis of each of the plate screws. FIG. 19 is a partial cross-section of the plate 310 taken along the medial axis of the linking section. FIG. 20 is first end view of the Beta™ version of the plate (with the k-wire ears) showing the laterally offset relationship of the two compression screw pockets or screw housings or shrouds.

FIGS. 21(*a*)-21(*v*) illustrate a method of performing a surgery using the dual pocket compression screw of the present invention as described herein after.

Figure 23:
FIG. 23 illustrates a compression screw.
Figure 22:
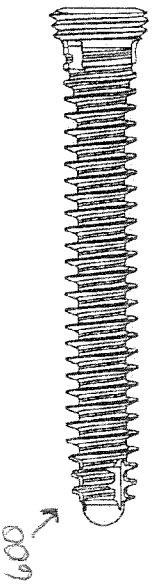
FIG. 22 illustrates a threaded locking screw 600, that can be used with the invention.
Figure 24:
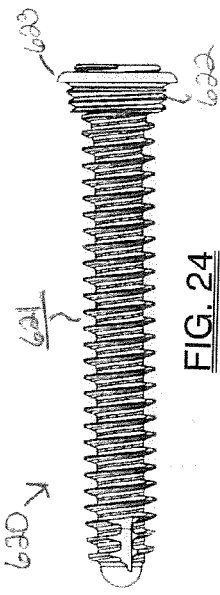
FIG. 24 illustrates a variable locking screw assembly.
Figure 25:
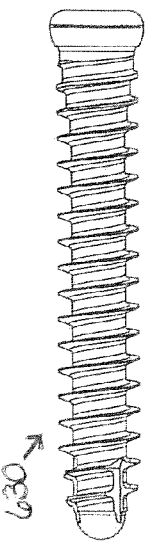
FIG. 25 illustrates a non-locking screw assembly.
Figure 26:
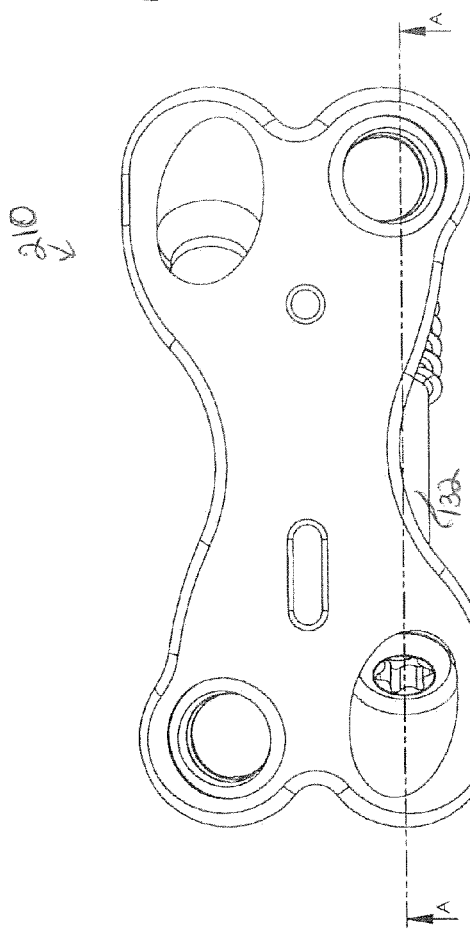
FIG. 26 illustrates a top view of an assembly of the plate.

FIG. 22 illustrates a threaded locking screw 600, that can be used with the invention, while FIG. 23 illustrates a compression screw 610, and FIG. 24 illustrates a variable locking screw assembly 620 including a screw 621 with a threaded head that locks into a locking insert 622 that comprises a material that is relatively deformable subject to the threads of the locking screw and that can be used with the present invention. FIG. 26 is the variation of the plate 210 from FIG. 12, with a compression screw 132 in position in the screw pocket, and FIG. 27 is a cross-section of FIG. 26 taken at line A-A illustrating how the screw head 134 is just received in the pocket so that it does not project substantially (i.e. less than 25%, and preferably 10% by volume) beyond the top surface of the plate and also does not sit too far below the bottom surface of the plate (i.e. less than 25%, and preferably 10% in depth at the short internal wall of the pocket).

In one method of causing locking of the screw relative to the plate, the screw 600 could include external screw threads 602 that mate with internal threads in the locking screw hole at a pre-selected angle, in some instances, the screw axis is perpendicular to a tangent at the top of the screw hole so that the screw axis angles slightly toward the bottom of the plate. However, other methods of causing locking could be employed, such as a variable locking assembly 622. The screw 610 used in the compression housing has a head 611 having a rounded rear shoulder 612 (such as a hemisphere, or a torroid), which allows for play in the convexly rounded recess in the compression housing. The compression is caused when the compression screw engages the bone and pulls the plate into that bone as it engages the internal face of surrounding the screw opening of the compression housing, and the k-wires and locking screw or screws act on their respective bone segment.

The screws useful with the plate of the present invention are self-starting, self-tapping screws including the option of partial or full cannulation. The screws include a cutting end having multiple flutes, and preferably 2 or 3 flutes about a conical recess, and preferably have a rounded end to avoid soft tissue irritation should they break an opposing cortical surface. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess.

The plate is formed of a biocompatible material, and preferably a metal such as surgical grade stainless steel, titanium or a titanium alloy. Preferably, the plate has a thickness of between about 1.0 and 2.0 millimeters, more preferably between about 1.2 and 1.8 millimeters, and most preferably between about 1.40 and 1.60 millimeters. The compression housing extends a depth below the bottom surface of the plate from about 3 to about 6 mm, preferably from about 4 to about 5 mm, and has a width of from about 3.5 to about 5.5, preferably from about 4 to about 5 mm., and a length of from about 3.0 to about 8.0, mm preferably from about 5.0 to about 7.0 mm. The opening in the upper surface of the plate for the compression opening is from about 4 to about 6 mm in width, and from about 5 to about 8 mm in length. The lower opening is about 2.5 to about 2.9 mm in diameter with a recess width of from about 2.5 to about 4.5 mm. The locking screw holes include a flat annular recess surrounding the threaded area that is about 6 mm in diameter. Both embodiments of the plate shown have a length of from about 25 to about 45 mm, preferably from about 28 to about 42 mm, and the compression screw axis forms an angle of from about 30° to about 45° to a longitudinal axis on the top of the plate. The plate includes a continuous outer edge, which is defined between the top and the bottom surfaces. In addition, the plate can include a small through holes sized to receive a K-wire or other similar guide wire.

Generally during the surgery the joints are first prepped which may include de-articulation between the bones to be fused. The bones are reduced, the plate is located such that all of the screws are aimed into the targeted bones and away from the joint, and the locking screw(s) and compression screw are inserted into a pre-drilled pilot holes and the compression screw is tightened into position. Further locking screws are screwed into adjacent bone segments. The plate is viewed radiographically. The incision is closed per the usual method.

The following is a description of a surgical technique for a cuboid calcaneal fusion procedure using the dual compression plate in accordance with the present invention.

In order to achieve compression with this plate, it is important to follow the correct order of operations. When proper technique is followed, the first pocket screw will generate compression across the joint. As is the case with any pocket plate, the plate must first be fixed on the same side of the hole as the pocket screw. As the first pocket screw is inserted, the bone will translate (compress) towards the unfixed aspect of the joint. In order for the plate to remain flush against the bone during compression, the empty pocket (or second pocket) must have space to slide within the prepared bone. The instruments provided are used to "over-countersink" for the second pocket screw, which allows the plate to translate within an over-sized bore, while maintaining a low-profile fit on the bone.

Figure 21E:
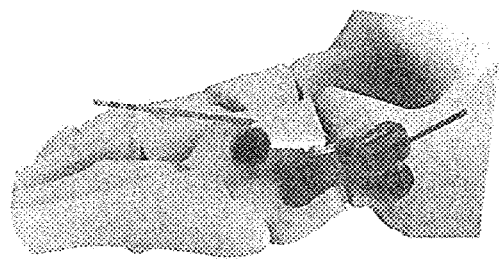
FIGS. 21(*a*)-21(*v*) illustrate of a method of performing a surgery using the plates and instruments in accordance with the invention.
Figure 21F:
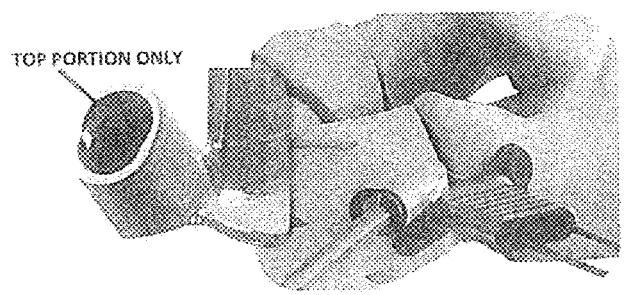
Figure 21G:
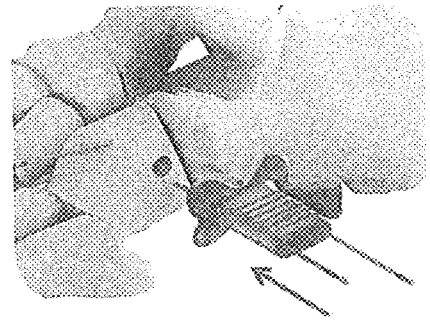
Figure 21H:
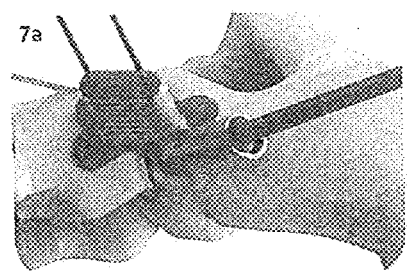
Figure 21I:
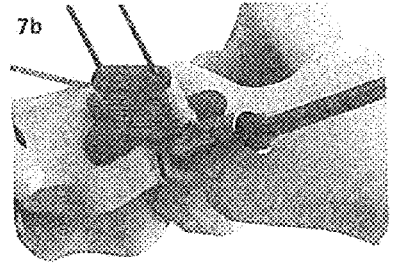
Figure 21J:
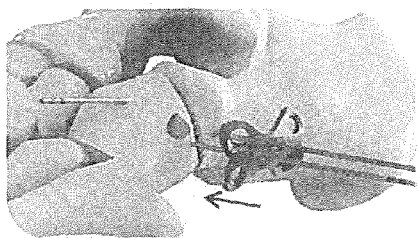
Figure 21K:
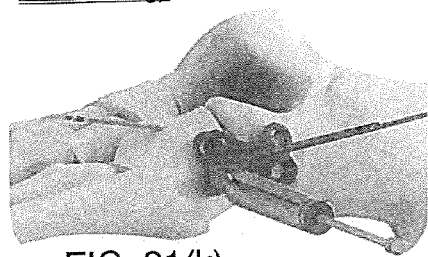
Figure 21L:
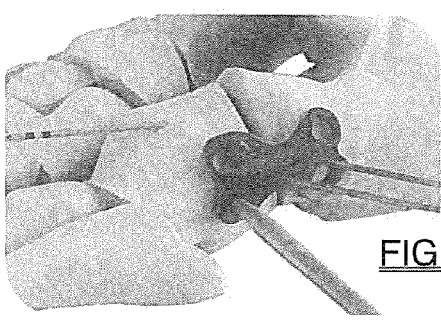
Figure 21M:
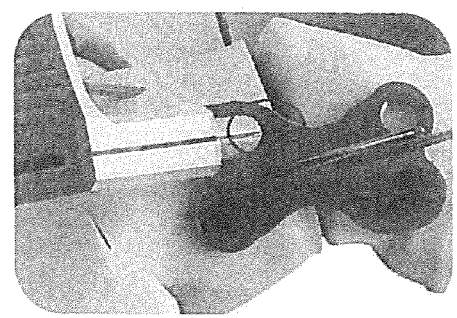
Figure 21N:
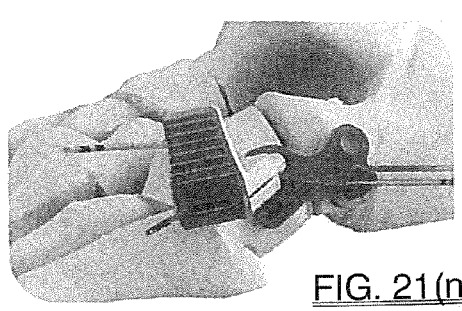
Figure 21O:
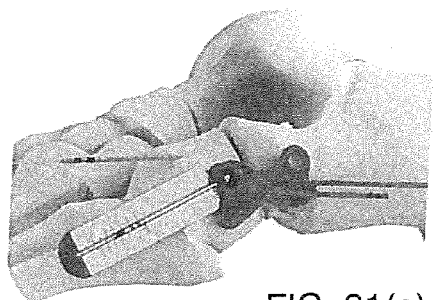
Figure 21P:
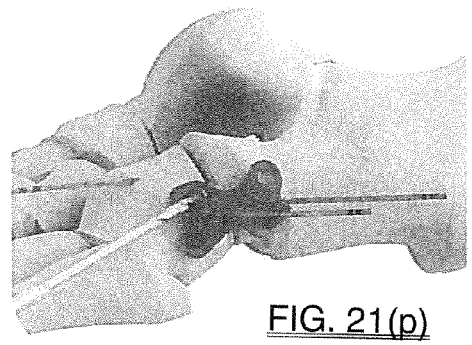
Figure 21Q:
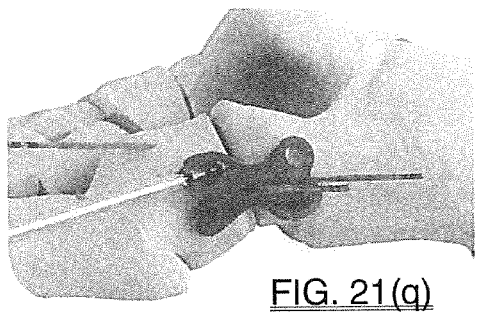
Figure 21R:
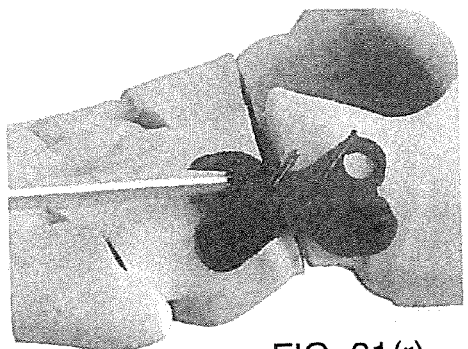
Figure 21S:
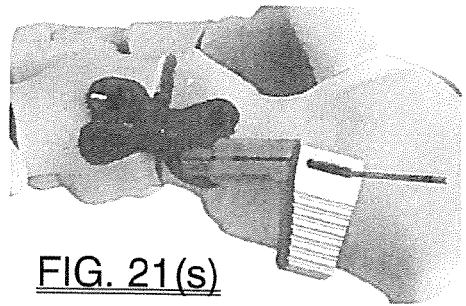
Figure 21T:
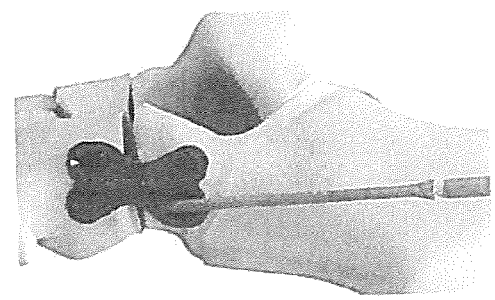
Figure 21U:
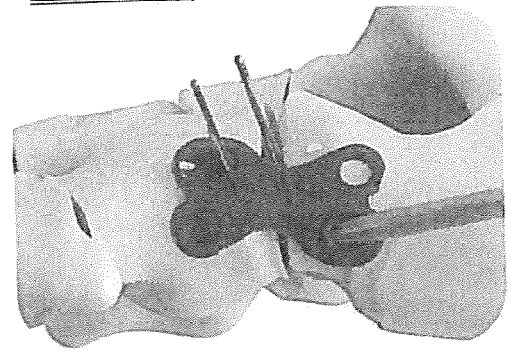
Figure 21V:
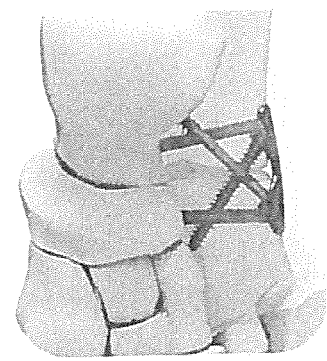

The countersink removes bone for the extra material on the underside of the pocket as shown in FIG. 21(a). Side 1, countersink through top portion only: Side 2, countersink through top and bottom portion. Fix Side 1. Insert primary compression screw (Pocket Screw 1). Insert primary compression screw (Pocket Screw 1).

Surgical Technique

This technique describes a calcaneal-cuboid fusion with distal-to-proximal compression.

The dual pocketLock plates can accommodate either a 4.0 mm partially threaded solid screw or a 4.0 mm cannulated screw in each pocket. 4.0 mm partially threaded solid screws are included in the dual pocketLock surgical caddy.

Step 1: Perform standard exposure and prepare the joint according to surgeon-preferred technique.

Step 2: Temporarily fix the joint in the desired orientation using the provided k-wires. When placing provisional fixation, be mindful of eventual plate and screw placement.

Step 3: Select the template that corresponds to the desired plate and place it over the joint. Plates and their corresponding templates are designated either as Alpha or Beta, indicating pocket location. All templates are marked with the plate length and orientation. For example, the 30 mm-long Alpha template is marked '30A', which matches the part number suffix on the corresponding '30A' plate.

Step 4: Insert a 1.4 mm k-wire through each k-wire hole in the template. Care must be taken to keep the wires parallel during insertion as they will later facilitate plate placement. Do not bend the wires.

Step 5: Select the provided countersink and drill through the template to prepare the first pocket. This will be the primary compression screw; countersink only through the top portion of the guide. Hold the template tightly against the bone and rotate the countersink until the shoulder of the countersink stops on the ledge inside of the guide.

Step 6: With the k-wires still in place, slide the template off the bone. Flip the template 180° and slide back over the wires to countersink for the second pocket. This pocket must be over-countersunk, as the plate will translate during insertion of the first (in this case, distal) pocket screw.

Step 7a: Rotate the countersink through the top portion of the guide until it stops on the ledge inside of the guide. Remove the countersink.

Step 7b: Insert the countersink through the bottom portion of the slot. Rotate until the countersink stops on the guide. The countersink will stop on the outside ledge of the guide rather than inside of the guide as in previous steps. 7

Step 8: Keeping the k-wires in place, remove the template by sliding it over the wires.

Step 9: Select the corresponding plate and slide it over the wires, positioning into the prepared bone pockets. The k-wire slot should be on the side of the over-countersunk pocket. The slot allows the plate to translate during compression.

Step 10: Using the fixed drill guide and the 2.4 mm drill bit, drill a pilot hole for the first locking screw (on the side of the k-wire hole). Take care to not move the plate after drilling for a locking screw in order to maintain the proper pilot hole alignment and prevent locking screw cross-threading. The threaded screw holes in the plate are compatible with a variety of screw options; 2.7 mm non-locking (gold), 3.5 mm non-locking or fixed-angle locking screws (magenta) and 4.0 mm non-locking screws (teal) are included in this or a related surgical set. Depending on surgeon preference, a combination of screw types can be used. 3.5 mm variable-angle locking screws may also be used in the plates; however the variable screw caddy must be present at the time of surgery. Reference the variable-angle locking screw technique guide (if variable-angle locking screws are desired.

Step 11: Determine the screw length required using the provided depth gage). The depth gage reading corresponds to the working length of the screw (from distal tip to underneath the screw head).

Step 12: Remove the desired screw from the screw caddy using the driver for all screws used throughout the procedure, verify the screw length using the gauge provided on the screw caddy.

Step 13: With the driver, insert the selected screw into the hole and drive the screw. A locking screw is recommended for this hole. Do not fully tighten the screw.

Step 14: Select the 1.4 mm Pocket Wire Guide and place the nose into the plate pocket, aligning the solid line on the guide with the line on the plate.

Step 15: With the guide fully seated in the plate pocket, insert a 1.4 mm guide wire through the guide at the desired trajectory. The pocket wire guide allows for 12° of planar angulation within the slot. Verify wire placement with fluoroscopy to ensure trajectory and screw purchase will be adequate.

Step 16: Remove the pocket wire guide and use the provided pocket depth gauge to measure over the wire and determine the required screw length. Subtract at least 2 mm from the depth gauge reading. Up to 4 mm of subtraction may be required based on compression generation.

Step 17: Use the 2.7 mm cannulated drill bit (drill over the wire for the 4.0 mm pocket screw. Drill all the way to the end of the wire to ensure the pilot hole is deep enough for the measured screw length.

Step 18: With temporary fixation still in place, Use the driver to insert the appropriate length 4.0 mm partially threaded screw through the pocket until almost fully seated in the pocket.

Step 19: Remove any provisional fixation wires and fully tighten the pocket screw. The proximal k-wire should remain in place during screw insertion to maintain plate alignment; the slot will allow plate translation during pocket screw insertion.

Step 20: Drill and insert the proximal locking screw using the technique described in Steps 11-14 above.

Step 21: Using the same technique as Steps 15 and 16 above, use the pocket wire guide and 1.4 mm k-wire to prepare for insertion of the second pocket screw. Verify wire position using fluoroscopy to ensure proper trajectory.

Step 22: Measure for the screw using the provided depth gage. Subtract approximately 2 mm from the depth gage reading. This screw will be a fully threaded 4.0 mm screw and will only achieve minimal additional compression.

Step 23: Using the 2.7 mm cannulated drill bit, drill over the wire to prepare a pilot hole for the pocket screw. Note that the pocket screw will be blunt-tipped, so be sure to drill all the way over the wire.

Step 24: Using the driver, insert the appropriate length fully threaded 4.0 mm non-locking screw.

Step 25: Remove all wires, fully tighten all screws and verify final position and joint alignment using fluoroscopy.

What is claimed is:

1. A plate and screw system which is capable of fixation of bone comprising a plate and a locking screw and a first and a second compression screw, the plate having a top surface opposing a bone facing surface in a z direction which opposes a bone surface, and the plate extending along a first length along a longitudinal axis and having a body extending along the longitudinal axis and defining a first end and a second end, the body defining a medial line, the first end having a terminal portion with a locking hole and the plate including a first and a second compression screw housing, each defining a compression screw hole extending at a compression screw angle relative to the longitudinal axis which angle is not 90°, wherein the compression screw angle of the compression screw hole of the first compression screw housing and the compression screw angle of the compression screw hole of the second compression screw housing are opposite with respect to the z direction, and at least one of the compression screw housings projecting from and beneath the bone facing surface of the plate.

2. A plate and screw system as set forth in claim 1, wherein the compression screw angle is from about 10° to about 70° relative to the longitudinal axis in the z direction.

3. A plate and screw system as set forth in claim 2, wherein the compression screw angle is from about 25° to about 60° relative to the longitudinal axis in the z direction.

4. A plate and screw system as set forth in claim 1, wherein at least one of the compression screw housings is peripheral to the medial line.

5. A plate and screw system as set forth in claim 1, wherein the locking screw is one of a plurality of locking screws, and wherein the first end of the plate defines a plurality of tabs, and at least one tab includes a threaded hole for a locking screw.

6. A plate and screw system as set forth in claim 5, wherein the first end and the second end each defines a tab which is longitudinally aligned with the second end so as to provide for bilateral mirror symmetry about the longitudinal axis.

7. A plate and a screw system as set forth in claim 1, wherein the plate includes a mid-section between the first end and the second end, and the mid-section includes the compression screw hole of the first compression screw housing offset between 20° and 40° from the compression screw hole of the second compression screw housing.

8. A plate and a screw system as set forth in claim 7, wherein the first and the second end each have two tabs one of which includes a locking hole and the other of which includes a compression housing.

9. A plate and a screw system as set forth in claim 7, wherein the first and the second end has only one tab for a screw hole and an aligned compression housing and the first end and the second end are linked through a diagonally extending linking section.

10. A plate and a screw system as set forth in claim 1 wherein the compression screw housing has a front surface which includes an opening for the compression screw, side and a bone facing surface which is connected to the front surface and to the bone facing surface of the plate so that the compression screw housing is closed to the bone surface.

11. A plate and a screw system as set forth in claim 10 wherein the compression screw has a head having a first diameter connected to a necked portion having a second diameter which is smaller than the first diameter and the opening for the compression screw is sized relative to first and second diameter so that the compression housing allows at least 5° of conical angulation of the compression screw in the compression housing.

12. A plate and a screw system as set forth in claim 11 wherein the opening for the compression screw is sized so that the compression housing allows at least 10° of conical angulation of the compression screw in the compression housing.

13. A plate and a screw system as set forth in claim 12 wherein the opening for the compression screw forms a slot which allows for linear angulation of the compression screw in the compression housing.

14. A plate and a screw system as set forth in claim 1 wherein both of the compression housings extend from the bone facing surface of the plate.

15. A plate and a screw system as set forth in claim 14 wherein both of the compression housings have openings through which a compression screw extends away from the bone facing surface of the plate.

16. A plate and a screw system as set forth in claim 15 wherein each of the openings extend from the bone facing surface of the plate in a direction that is not perpendicular to the bone-facing surface of the plate.

\* \* \* \* \*